United States Patent [19]

Rosen

[11] Patent Number: 4,520,134
[45] Date of Patent: May 28, 1985

[54] N-ALKYL-4'-HYDROXYACETANILIDES, PHARMACEUTICAL COMPOSITIONS COMPRISING THEM AND THEIR USE

[76] Inventor: Gerald M. Rosen, 403 Knob Ct., Chapel Hill, N.C. 27514

[21] Appl. No.: 601,774
[22] PCT Filed: Aug. 26, 1983
[86] PCT No.: PCT/US83/01311
§ 371 Date: Apr. 6, 1984
§ 102(e) Date: Apr. 6, 1984
[87] PCT Pub. No.: WO84/00886
PCT Pub. Date: Mar. 15, 1984

Related U.S. Application Data

[63] Continuation-in-part of Ser. No. 412,313, Aug. 27, 1982, abandoned.

[51] Int. Cl.$^3$ .................. A61Y 31/165; C07C 103/38
[52] U.S. Cl. ..................................... 514/625; 564/223
[58] Field of Search ........................ 424/324; 564/223

[56] References Cited

PUBLICATIONS

Hinsberg et al., Arch. Exp. Pathol. Pharm., 33: 216–250 (1894).

*Primary Examiner*—Stanley J. Friedman
*Attorney, Agent, or Firm*—Millen & White

[57] ABSTRACT

N-alkyl-4'-hydroxyacetanilides wherein alkyl is of up to 8 carbon atoms, preferably ethyl or isopropyl, have analgesic, antipyretic, anti-inflammatory and sedative activity. Those of at least two carbon atoms lack the hepatotoxicity of acetaminophen and the N-methyl compound also has substantially less hepatotoxicity than acetaminophen. Pharmaceutical compositions comprising them are employed to ameliorate pain, reduce fever, reduce the symptoms of systemic inflammatory conditions and sedate.

21 Claims, No Drawings

N-ALKYL-4'-HYDROXYACETANILIDES, PHARMACEUTICAL COMPOSITIONS COMPRISING THEM AND THEIR USE

CROSS REFERENCE TO RELATED APPLICATION

This application is a continuation-in-part of application Ser. No. 06/412,313 filed Aug. 27, 1982, now abandoned.

BACKGROUND OF THE INVENTION

1. Field of the Invention

This invention relates to novel pharmaceutical compositions of matter comprising N-alkyl-4'-hydroxyacetanilide, which have analgesic, antipyretic, antiinflammatory and sedative activity, but lack the nephrotoxicity and hepatotoxicity of acetaminophen. This invention further relates to a method of ameliorating pain through the administration of these compounds.

2. Description of the Related Art

Acetaminophen (paracetamol) has become increasingly popular as an analgesic, despite the fact that its heptatoxicity has been documented since 1966. D. G. Davidson and W. N. Eastham, *British Medical Journal* 2:497–499 (1966). It has recently been shown that chronic ingestion of therpeutically recommended doses of acetaminophen in humans for extended periods of time can cause massive hepatic necrosis. A. J. Ware, et al., *Annals of Internal Medicine* 88:267–268 (1978); D. M. Rosenberg and F. A. Neelon, *Annals of Internal Medicine* 88:129 (1978); J. D. Barker, Jr., *Annals of Internal Medicine* 87:299–301 (1977) and G. K. Johnson and K. G. Tolman, *Annals of Internal Medicine* 87:302–303 (1977). Individuals with underlying liver injury or disease have been found to be particularly susceptible to acetaminophen-mediated hepatotoxicity. D. M. Rosenberg, et al., *Southern Medical Journal* 70:600–601 (1977); H. L. Bonkowsky, et al., *Lancet* 2:1016–1018 (1978); V. Schoenfeld, et al., *New England Journal of Medicine* 303:47 (1980); and D. P. Golden et al., *Oral Surgery* 51:385–389 (1981). Additionally, conditions which induce the liver enzymes responsible for the metabolization of acetaminophen, such as consumption of alcohol or barbituates, will markedly potentiate the heptatoxicity of this compound.

Studies by Nebert with inbred mice have suggested that acetaminophen can cause cataracts in humans. *Science,* 200:539–541 (1978). Acetaminophen has also recently been implicated as a possible human carcinogen. M. I. Mihatasch, et al., *Schweizerische Medizonische Wochenschrift* 110:255–264 (1980). Thus, acetaminophen, which is an ubiquitious component of over-the-counter and prescription drugs, may present a serious risk to general users and sensitive user subpopulations in terms of its hepatic and other toxic effects.

The mechanism of acetaminophen toxicity is not fully understood in the prior art. Editorial, *Lancet* 2:1189 (1975); B. E. Walker, et al., *Clinical Science & Molecular Medicine* 47:449–459 (1974). However, recent studies, which are discussed infra, suggest the involvement of certain hepatic enzyme systems which convert acetaminophen into a toxic metabolite or produce a toxic by-product.

Because such diverse compounds as cysteamine, methionine, cysteine, dimethlymercaptol, selenium and vitamin E have afforded varying degrees of protection in man and experimental animals against the hepatoxicity of acetaminophen, and because these compounds under certain circumstances can act as antioxidants, it has been suggested that other antioxidants would also provide protection. J. Kelleher, et al., *Journal of Internal Medical Research* 4, Supplement (4):138–144 (1976). Compounds such as 2-methylthiazolidine-4-carboxylic acid which form cysteine in the liver can also protect against heptotoxins. *Chemical & Engineering News,* Aug. 2, 1982 at p. 18.

Animal studies indicate that antioxidants can provide limited protection against the hepatotoxic effects of acetaminophen. For example, α-tocopherol protects vitamin E deficient rats. B. E. Walker, et al., supra; J. Kelleher, et al., supra. It has been reported that vitamin C may also provide such protection. T. C. Raghuram, et al., *Toxicology Letters* 2:175–178 (1978).

U.K. patent application No. 2,040,164 and U.S. Pat. No. 4,292,298 (assigned to Beecham Group Ltd.), both claim compositions and methods for reducing the acute liver toxicity effects of acetaminophen by the oral administration of a co-formulation with ascorbic acid. The U.S. patent discloses that 300 mg/kg of ascorbic acid in nonsustained release form had no protective effect against 450 mg/kg (orally) of paracetamol whereas the same amount of ascorbic acid in sustained release form had substantial protective effect and 600 mg/kg and even greater effect.

However, in an experimental study in man, although vitamin C caused a rapid and pronounced decrease in the excretion rate of acetaminophen sulfate, it did not affect the apparent half-life of the drug, as evidenced by its rate of secretion as such in the urine, or as glycuronide or its sulfate. J. B. Houston and G. Levy, *Journal of Pharmacetical Science* 65:1218–1221 (1976). It was stated that the specific interaction between acetaminophen and ascorbic acid was probably of little clinical significance under usual conditions; that is, when acetaminophen is taken in single recommended doses as an analgesic or antipyretic. Other researchers concluded that the protective effects manifested by these vitamins cannnot be attributed to their anti-oxidant activity, because whereas vitamin E and propyl gallate reduce heptatotoxicity, diphenyl-p-phenylene-diamine (DDPD), an antioxidant in vitro and one which give protection against CCl$_4$ hepatotoxicity, enhances acetaminophen hepatotoxicity. J. Kelleher et al., supra. These authors speculated that the modification of hepatotoxicity may result from an alteration in the activity of specific components of the microsomal drug-metabolizing enzyme systems.

Suprisingly and notwithstanding the published literature reporting that some antioxidants may provide protection against the heptatoxic effects of acetaminophen, I have found that the omnipresent antioxidants BHT (butylated hydroxytoluene) and BHA (butylated hydroxyanisole), which have been used in foods to prevent spoilage, profoundly enhance its hepatotoxicity. Because the general population ingests large amounts of these chemicals daily due to their presence in a wide variety of food products, the likelihood of an increased incidence of hepatotoxicity in persons taking repeated dosages of acetaminophen is self-evident.

Other approaches to ameliorating acetaminophen-mediated hepatotoxicity have also been considered. For example, a news release quoted a publication in "The Medical Letter" which reported a clinical study showing that N-acetylcysteine is effective in preventing hepatotoxicity if administered with in 16 hours after an overdose. *Washington Post,* Dec. 7, 1979, page A9. The authors chose N-acetylcysteine because of its chemical similarity to glutathione, the substantce which the body employs to detoxify the drug.

Dimethyl sulfoxide (DMSO) has been shown to protect mice against the hepatotoxic effects of acetaminophen when administered up to one hour after administration of acute toxic amounts of acetaminophen. C. P. Seigers, *Journal of Pharmacology* 30:375-377 (1978). Its activity was attributed to inhibition of microsomal oxidation of the drug by the the hepatic mixed-function oxidase system due to chemically reactive alkylating agents. On the other hand, this theory would fall to explain the inability of DMSO to protect mice against $CCl_4$ hepatotoxicity, since this compound is also activated by the mixed function oxidase system. The authors therefore were unable to provide the acetaminophen-antihepatotoxic mechanism of DMSO.

It is apparent from the foregoing that an effective method of protecting humans against acute acetaminophen hepatotoxicity had not been established by the prior art. Furthermore, it may be preferable to restrict the use of acetaminophen per se, rather than merely administering it concurrently with an ameliorating agent. Like so many other toxic chemicals, once the mechanism by which acetaminophen initiates hepatotoxicity is understood, the potential risk to human health from acute and chronic exposure to this drug can be better assessed and avoided.

The risk of severe hepatic damage is high in patients who take acetaminophen in combination with drugs that are known to induce cytochrome P-450 (the enzyme responsible for the bioactivation of acetaminophen to its toxic intermediate). N. Buchanan and G. P. Moodley, *British Medical Journal* 2:307-308 (1979); N. Wright and L. F. Arthurs and J. F. Fielding, *Journal of the Irish Medical Association* 73:273-274 (1980). Alcohol has been demonstrated to induce cytochrome P-450, P. S. Misra, et al., *American Journal of Medicine* 51:346-351 (1971), so it is not surprising that acetaminophen-mediated hepatotoxicity is markedly increased by chronic use of ethanol. D. J. Emby and B. N. Fraser, *South African Medical Journal* 51:208-209 (1977); R. Goldfinger, et al., *American Journal of Gastrology* 70:385-388 (1978); C. J. McClain, et al., *Journal of the American Medical Association* 224:251-253 (1980); and H. Light, et al., *Annals of the Internal Medicine* 92:511 (1980).

At the present time, there are over 300 drugs in use that have been shown to induce cytochrome P-450, and in doing so should promote the hepatotoxicity of acetaminophen. For example, the well-known cytochrome P-450 inducer, phenobarbital, is an effective and widely prescribed drug for certain types of epilepsy. Therefore, the chronic use of acetaminophenin individuals with grand mal should be contraindicated. Although tobacco is also known to induce cytochrome P-450, W. J. Jusko, *Drug Metabolism Reviews* 9:221-236 (1979), at present, there is no information indicating whether or not smoking promotes the toxicity of acetaminophen.

In 1973, Mitchell and co-workers published a series of papers which demonstrated that cytochrome P-450 participates in the activation of acetaminophen to its toxic intermediate. J. R. Mitchell, et al., *Journal of Pharmacology and Experimental Therapeutics* 187:185-194 (1973); D. J. Jollow, et al., *Journal of Pharmacology and Experimental Therapeutics* 187:195-202 (1973); and W. Z. Potter, et al., *Journal of Pharmacology and Experimental Therapeutics* 187:203-217 (1973). Nevertheless, the nature of this metabolite and the mechanism by which acetaminophen initiates hepatotoxicity were not established.

It was originally proposed that cytochrome P-450 oxidizes acetaminophen to N-hydroxyacetaminophen, which then loses water to give the hypothesized intermediate N-acetyl-p-benzoquinone imine. If this intermediate is produced, it could be detoxified by reaction with reduced glutathione (GSH) to yield 3-(glutathion-S-yl)-acetaminophen. J. A. Hinson, et al., *Drug Metabolism Disposition* 10:47-50 (1982); however, when GSH is depleted, this quinone imine binds to cellular macromolecules. W. Z. Potter, et al., *Pharmacology* 12:129-143 (1974). Based on these findings, it has been proposed that covalent binding of N-acetyl-p-benzoquinone imine to intracellular macromolecules is responsible for the cell death that is manifested as hepatic injury. Potter, et al., supra. Recent studies by J. A. Hinson, et al., *Life Science* 24:2133-2138 (1979) and S. D. Nelson, et al., *Biochemical Pharmacology* 29:1617-1620 (1980) cast doubt on aspects of this mechanism. These investigators have demonstrated that if N-acetyl-p-benzoquinone imine is the toxic species, it is biosynthesized by a pathway that does not include N-hyroxyacetaminophen.

An alternative hypothesis to account for the formation of N-acetyl-p-benzoquinone imine envisions the epoxidation of acetaminophen followed by ring opening with loss of water. If such a mechanism were correct, then the addition of heavy oxygen ($O^{18}2$) to the reaction mixture would lead to the incorporation of $O^{18}$ into half of the N-acetyl-p-benzoquinone imine. However, when such a study was conducted, the investigators were unable to detect $O^{18}$ in any of the acetaminophen metabolites, S. D. Nelson, et al., supra; and J. A. Hinson, et al., *Drug Metabolism Disposition* 8:289-294 (1980).

A third mechanism suggests that cytochrome P-450 initiates a one-electron oxidation of acetaminophen, giving acetaminophen free radical. S. D. Nelson, et al., *Molecular Pharmacology* 20:195-199 (1981). Transfer of an electron from this free radical to oxygen would produce a superoxide free radical and N-acetyl-p-benzoquinone imine. Support for such an hypothesis and for the participation of this reaction pathway in hepatotoxicity comes from the observation that acetaminophen can be oxidized to a free radical which exhibits all of the electrophilic properties assigned to the hypothetical toxic intermediate. S. D. Nelson, et al., *Molecular Pharmacology* 20:195-199 (1981). The possibility of a free radical mechanism of hepatotoxicity is further supported by the demonstration that promethazine, A. E. M. McLean and L. Nuttall, *Bio-chemical Pharmacology* 27:425-430 (1978); glutathione, M. Strolin-Beneditte, et al., *Journal of Pharmaceutics and Pharmacology* 27:629-632 (1975), and A. R. Burkitt, et al., *Biochemical Pharmacology* 28:2941-2946 (1979); and β-dimethylaminoethanol, C. P. Siegers and M. Young, *Arzneimittel Forschung* 29:520-523 (1979), which are known free radical scavengers, afford protection against acetaminophen toxicity.

I have found that acetaminophen-mediated chronic and acute hepatotoxicity is due to the formation of superoxide free radicals, according to what I believe to be the following mechanism:

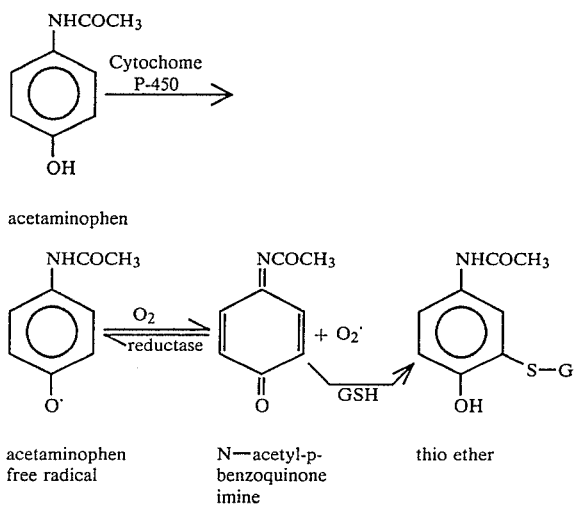

acetaminophen acetaminophen free radical

N—acetyl-p-benzoquinone imine thio ether

Acetaminophen is metabolized by first being converted to the acetaminophen free radical by cytochrome P-450. This toxic free radical is oxidized to N-acetyl-p-benzoquinone imine, which is normally eliminated by conversion by glutathione in the liver to the glutathione-acetaminophen thiether. The oxidation of the acetaminophen free radical to N-acetyl-p-benzoquinone imine produces the toxic superoxide free radical which is dismuted to $H_2O_2$, which is eliminated by peroxidase enzymes. However, when there are insufficient glutathione levels in the liver to react with the N-acetyl-p-benzoquinone imine produced by this mechanism, it can be reconverted by reductase to the acetaminophen free radical while thus generating additional toxic superoxide free radical. This cyclic regeneration of the acetaminophen free radical generates sufficient superoxide free radical to overwhelm the naturally occurring superoxide dismutase (SOD), thereby promoting hepatotoxicity through lipid peroxidation.

In my U.S. Pat. No. 4,314,989, I disclosed methods and compositions for preventing acetaminophen-induced hepatotoxicity by employing methionine sulfoxide to destroy the toxic acetaminophen free radical before it has the opportunity to react with oxygen.

The present invention is based on my finding that certain N-alkyl-4'-hydroxyacetanilide compounds possess analgesic activities comparable to acetaminophen but lack its nephrotoxicity and hepatotoxicity. These compounds are not metabolized by the liver enzyme reactions in a manner which produces the toxic intermediate superoxide free radical.

Certain members of this genus are disclosed as starting materials for other compounds having uses unrelated to analgesia in British Pat. No. 749,907 (1956), and at Chemical Abstracts 51:1265i. In 1894, O. Hinsberg and G. Treuple, *Archives of Experimental Pathology and Pharmacology* 33:216–250 (1894), synthesized a number of p-amidophenols and examined their antipyretic and analgesic activities. Among the tested compounds was N-ethyl-4'-hydroxyacetanilide. In this paper, the authors presented data on its antipyretic activity, however, they concluded that this compound had no antipyretic activity. They also stated, without supporting data, that N-ethyl-4'-hydroxyacetanilide had no analgesic properties. This is contrary to my findings using an accepted hot plate analgesic model. In that same year, German Pat. No. 79,098 was granted to A. M. Hochst for the synthesis of N-ethyl-4'-hydroxyacetanilide. The patent states that the products are useful as medicaments, without identifying the conditions for which it might have utility or any methods of use. In 1899, Hinsberg, *Liebig's Annual* 305:276–289 (1899) published a more detailed synthesis of N-ethyl-4'-hydroxyacetanilide than is found in his 1894 paper. No biological activity is discussed in this article.

It is the object of this invention to provide novel pharmaceutical compositions which have acetaminophen's analgesic activity, but are nonhepatotoxic; and further, to provide methods for their use. A further object is to provide novel N-alkyl-4'-hydroxyacetanilides.

SUMMARY OF THE INVENTION

In a composition aspect, this invention relates to pharmaceutical compositions comprising in unit dosage form, an analgesic effective amount per unit dosage of an acetanilide of the formula

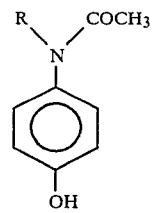

wherein R is alkyl of up to 8 carbon atoms, in admixture with a pharmaceutically acceptable carrier. Such compositions are preferably adapted for oral ingestion and most preferably are in the form of tablets or capsules.

In another composition aspect, this invention relates to novel species of N-alkyl-4'-hydroxyacetanilides, including N-isopropyl-4'-hydroxyacetanilide.

In a method of use aspect, this invention relates to a method of ameliorating pain which comprises administering to a human being in pain an analgesically effective amount of a composition of this invention.

In a second method of use aspect, this invention relates to a method of reducing fever which comprises administering to a human being with an elevated temperature an antipyretically effective amount of an acetanilide of this invention.

In a further method of use aspect, this invention relates to a method of ameliorating systemic inflammatory conditions which comprises administering to a human being with a systemic inflammatory condition an anti-inflammatory effective amount of acetanilide of this invention.

In still another method of use aspect, this invention relates to a method of sedating human beings which comprises administering thereto a sedative effective amount of an acetanilide of this invention.

DETAILED DISCUSSION

In order to be commercially acceptable for use by the general public, an analgesic and antipyretic compound must be (a) non-toxic, that is, it must be substantially free from any significant toxic effects at its therapeutic dosage;

(b) stable, that is, have a shelf-life of at least six months, preferably at least one year, and more preferably at least two years in conventional pharmaceutical forms, that is tablets, capsules, pills, elixirs and other aqueous vehicles;

(c) non-volatile, that is, a liquid or preferably a solid exhibiting no significant vapor pressure under ambient conditions;

(d) substantially free of subjective symptomology, that is, which do not produce significant symptoms detectable to the person ingesting the analgesic; and (e) nonhepatotoxic, that is, its metabolization does not result in production in the liver of the toxic superoxide free radicals or other toxic metabolites.

The N-alkyl-4'-hydroxyacetanilide compounds employed in the compositions of this invention meet all of the above criteria. In addition to their analgesic activity, these compounds are effective antipyretics in the same administered dosages. They also possess systemic anti-inflammatory activity and, at higher doses, sedative activity.

In the compounds of this invention, the acetamido nitrogen atom preferably bears an alkyl group of 2–8 carbon atoms which blocks metabolic conversion of the compound into the toxic acetaminophen metabolite. Examples thereof are those wherein R is ethyl or polycarbon alkyl, e.g., propyl, butyl, amyl, hexyl, heptyl, or octyl, each being straight, or branched chain, preferably those of 2–4 carbon atoms. As stated above, less preferably R can also be methyl.

The compounds of this invention can be employed as such or as a salt thereof, e.g., Na, K, with a strong base, particularly when greater water solubility is desired. These salts can be prepared by mixing the free base with an aqueous solution of a molar equivalent of sodium or potassium hydroxide or by adding a molar equivalent of sodium or potassium ethoxide in an anhydrous organic solvent solution of the freebase.

Comtemplated equivalents of the compounds employed in the compositions of this invention are those bearing another R-group which blocks metabolic conversion of the compounds into the toxic acetaminophen metabolite. Because the blocking activity of the group, rather than its exact chemical structure, is critical to this invention, it will be apparent to those skilled in the art that other R-groups can meet the criterial listed hereinabove. Examples of such R-groups are other hydrocarbon groups, as, for example, higher alkyl, such as of 9–16 carbon atoms; cycloalkyl, such a cyclopropyl, cyclopentyl, and cyclohexyl; and the unsaturated analogs of each. Generally speaking, the latter are less preferred. Additionally, the N-hydrocarbon group can also bear a simple substituent which does not interfere with the compound's analgesic activity. Some position isomers bearing an N-substituted acetamido groups which is positioned ortho or meta rather than para, as in the compounds of this invention, may also meet the above-listed criteria.

In order to become nephrotoxic and hepatotoxic, they must first be converted in vivo to acetaminophen and then metabolized to a toxic free radical. In the case of N-methyl-4'-hydroxyacetanilide, this compound must be N-demethylated to form acetaminophen. N-demethylation of an amine is not very difficult, but N-demethylation of an amide (as in this case) is more difficult and, since competing reactions are continually taking place, only a limited quantity of acetaminophen is formed. Thus, a smaller quantity of the toxic metabolite is ultimately produced than is the case when acetaminophen is given directly. Although the analgesic use of the N-methyl-4'-hydroxyacetanilide affords a reduced risk of toxicity when compared with acetaminophen, its degree of protection is less complete than that of those N-alkyl-4'-hydroxyacetanilide compounds of this invention in which alkyl is larger than methyl. The best documented N-demethylation of an amide in humans is diazepam, which produces N-desmethyldiazepam. However, in the case of N-ethyl-4'-hydroxyacetanilide, for example, N-deethylation of an amide is rare (if ever seen) and thus, no acetaminophen is formed by oxidative N-deethylation.

The following is an animal study which verifies the utility of the claimed compounds as analgesics.

Two groups of mice, six mice per group, were used in the hot plate test described by S. I. Ankier *European Journal of Pharmacology* 27:1–4 (1974). The control group, which was untreated, at a plate temperature of 54° C. took an average of 44 seconds to lick a back paw. The test group received a dose of N-ethyl-4'-hydroxyacetanilide (30 mg/kg) administered intraperitoneally, and when placed on the hot plate at 54° C. 10 minutes later, shown an average time of 64 seconds before licking a back paw. The analgesic activity of this compound thus increased the pain-response time by almost 50 percent.

A further experiment showed the compound's lack of hepatotoxicity as compared with acetaminophen. Three groups of DBA/2H mice, a strain which is known to be resistant to acetaminophen hepatotoxicity, received intraperitoneal administrations of acetaminophen (400 mg/kg in aqueous vehicle), or N-ethyl-4'-hydroxyacetanilide (500 mg/kg in propylene glycol), or received saline only as a control group. (The $LD_{100}$ dose of acetaminophen is 400 mg/kg in some sensitive strains of mice; for example, outbred Swiss army mice.) No immediate symptomatic effects were noted in the acetaminophen-dosed mice. N-ethyl-4'-hydroxyacetanilide-dosed mice showed sedative effects, that is ataxia of the hind legs after about 15 minutes and drowsiness after about 25 minutes, which lasted for about one-half hour. At an oral dose of 600 mg/kg of the same compound (aqueous vehicle, pH 12), the mice went to sleep for about 25–40 minutes. After 24 hours, all three groups of mice were sacrificed. Upon histopatho-logical examination of liver sections, the control and N-ethyl-4'-hydroxyacetanilide groups (both i.p. and oral) exhibited no fatty changes and no other signs of hepatotoxicity; whereas the acetaminophen group showed severe hepatic necrosis (an estimated 60% of the liver was necrotic). The oral $LD_{50}$ dose of acetaminophen is about 400 mg/kg; at which dose severe hepatotoxicity is manifested. In a similar experiment, mice treated with N-methyl-4'-hydroxyacetanilide (400 mg/kg) showed prenecrotic hepatic lesions, thus evidencing an incomplete level of protection.

The toxicity of N-isopropylacetaminophen was evaluated by injecting mice with this compound at various doss from 100–400 mg/kg, i.p.) and 24 hours later, the animals were sacrificed and histopathology was determined for the liver, kidney and lung. In all cases, no organ showed any signs of injury.

Of interest was the finding that at the higher doses (250–400 mg/kg, i.p.) all the mice demonstrated significant CNS sedation. The higher the dose, the longer the sedation. This was also found to be the case when mice were given the drug orally, except the dose needed to give the same sedative activity was higher (400–600 mg/kg, oral). This sedative effect of the drug lasted from 30 min. at 250 mg/kg to approximately 1.5 hr at 400 mg/kg. At the higher dose, the mice went to sleep. Once the mice recovered from this sedative effect, no additional CNS effects were observed.

The analgesic properties of N-isopropylacetaminophen were tested using the hot plate test described by Ankier (*Eur. J. Pharmacol.* 27: 1–(1974)). Two groups of mice, 6 animals/group were used. The first group was placed on the hot plate, individually, and time need to lick the back paw was recorded and found to be 44 seconds (average) at 54° C. The second group of mice each received 30 mg/kg (i.p.) N-isopropylacetaminophen and after 10 minutes placed on the hot plate at 54° C. The time required to lick the rear paw was measured and found to be 64 seconds (average), thus increased response time by 50%.

PREPARATION AND USE

The compounds used in the claimed compositions can be synthesized following the procedures described in the prior art cited above. I have also prepared both N-ethyl and N-isopropyl-hydroxyacetanilide as follows:

Preparation 1

To a solution of 5 g (0.0459 moles) of p-aminophenol in 50 ml dimethylformamide (DMF), was slowly added 8.67 ml (0.0917 moles) of acetic anhydride. The reaction mixture was heated at 60° for three hours, and then poured over crushed ice. A solid precipitate was filtered out. The remaining liquid was extracted with chloroform, dried over anhydrous magnesium sulfate and evaporated to dryness. The remaining liquid was poured over crushed ice. A solid precipitated. All solid material was combined and dried, yielding 5.5 g of 4'-acetoxyacetanilide.

Five g of this 4-acetoxyacetanilide (0.0259 moles) was dissolved in 200 ml of dry tetrahydrofuran (THF). To this mixture was added slowly, over one-half hour, 1.97 g (0.0518 moles) of lithium aluminum hydride. After the addition of this reagent, the reaction was refluxed for three hours, cooled, and saturated ammonium chloride solution was slowly added. The resultant mixture was filtered, evaporated to dryness and the remaining oil was dissolved in dilute HCl. This solution was extracted with chloroform several times. The remaining aqueous phase was made basic with sodium carbonate to achieve approximately pH 10 and extracted once again with chloroform. The chloroform solution was dried over anhydrus magnesium sulfate and evaporated to dryness. This acid/base extraction procedure was repeated several time to yield 2.2 g of p-ethylaminophenol, as an oil which solidified upon standing.

Two g of p-ethylaminophenol (0.0146 moles) were dissolved in 50 ml DMF. To this was added 2.98 g of acetic anhydride (0.0292 moles). The mixture was heated at 60° for three hours and then poured over crushed ice. Sodium carbonate was added until a pH of approximately 10 was achieved. The solution and precipitated oil were extracted with chloroform, dried over anhydrous magnesium sulfate, and then evaporated to dryness leaving a residual oil. To this oil was added 5% sodium hydroxide, and the mixture was heated at 60° for one hour. The solution was cooled and then extracted with chloroform. The remaining aqueous phase was acidified with dilute HCl to achieve a pH of approximately 4, and then extracted with chloroform. The liquid was dried over anhydrous magnesium sulfate, and then evaporated to dryness. The residual brown solid material was recrystallized from an ethanol-water mixture to yield N-ethyl-4'-hydroxyacetanilide (melting point 183°–185° C.).

Preparation 2

Twenty-five g (0.18 moles) of p-nitrophenol and 58 g (1 mole) of acetone were mixed together and catalytically reduced using hydrogen and platinum oxide until hydrogen was no longer taken up. The work-up followed the procedure of Majors (*J. Amer. Chem. Soc.* 31:1901–1908 (1931), giving 11 g (41%) of N-isopropyl-p-hydroxyaniline, m.p. 143° C.

Ten g (0.066 moles) of N-isopropyl-p-hydroxyaniline was dissolved in 50 ml acetic acid and to this mixture was added 13.5 g (0.132 moles) of acetic anhydride. This reaction was heated to 50° C. for 5 hours, then poured over crushed ice. Sodium carbonate was added until the pH was approximately 8.5, then the solution was extracted with chloroform, dried over anhydrous magnesium sulfate, and evaporated to dryness giving an oil which immediately was placed into 10% sodium hydroxide and warmed to 70° C. for 5 hours. Upon cooling, the mixture was extracted with chloroform, then made acidic with 10% HCl until the pH of the solution was 2–3. The solution was then extracted with chloroform, dried over anhydrous magnesium sulfate, and evaporated to dryness giving 7.6 g (60%) of N-isopropyl-4'-hydroxy-acetanilide as a white solid that was recrystallized from water, m.p. 152°–153° C. I.R. 3300–3200 cm$^{-1}$ (—OH) and 1660 cm$^{-1}$ (amide carbonyl). The sodium salt of this compound was prepared by reacting an equal molar quantity thereof with sodium hydroxide in water. The water was evaporated to dryness leaving the sodium salt as a solid which was dried further, m.p. 52°–54° C.

Substituting other p-alkylaminophenols, for example, p-n-propylaminophenol, p-octylaminophenol, for the p-ethylaminophenol in the former preparation and other N-alkyl-p-hydroxyanilines for the N-isopropyl-p-hydroxyaniline in the latter preparation produces the other N-alkylacetanilides employed in this invention. They can be produced according to the methods described in British Pat. No. 749,907 (1956), whose disclosure is incorporated herein by reference.

The acetanilides of this invention are preferably formulated in unit dosage form, preferably in admixture with a pharmaceutically acceptable carrier. The compositions of this invention contain, per unit dosage, an analgesic effective amount of an acetanilide of the formula given hereinabove, i.e., an amount effective to ameliorate simple, non-intractible pain, e.g., the pain relieved by aspirin, acetaminophen or other antipyretic analgesics, for example, the pain of headaches, arthritis, influenza, colds, simple sprains, strains and other minor trauma, in at least a small human being (10 kg), for example, 25 mg (infant dosage) to 750 mg (adult dosage), preferably 100 to 500 mg per unit dosage, preferably per oral unit dosage. The compositions can be in the form of sterile injectable powders and solutions, suppositories, buccal and preferably oral dosage forms, for example, pills, tablets, capsules, dragees, sweetened syrups and elixirs. Tablets, capsules and oral aqueous solutions are preferred. Preferred formulations are those commonly used by persons who are skilled in the pharmaceutical art, most preferably those used for the administration of acetaminophen.

The acetanilides of this invention are administered to human beings in an analgesic, antipyretic, anti-inflammatory or sedative effective amount, that is, an amount effective to ameliorate simple pain as described above in a human suffering therefrom; to lower body temperature in a human being with a fever; to reduce the symptoms of systemic inflammation in a human being suffering therefrom, for example, arthritics; or to sedate a human being. Significant sedative effects are manifested only at dosages substantially higher than that required to achieve analgesic, antipyretic and anti-inflammatory effects, for example, at dosages from 3 to 5 times higher. Although this invention is directed in its method of use aspect primarily to the treatment of human beings, as will be apparent to those skilled in the art, the acetanilides of this invention can also be administered to other species of mammals suffering from similar ailments or to sedate them. The individual and daily dosage rates correspond generally to those employed for acetaminophen. The preferred rate of administration is about 5 mg/kg to 15 mg/kg. When adminstered orally, the rate of administration is preferably 150–500 mg per dosage for children and about 300–1,000 mg per dosage for adults, repeated as required up to about 6 times daily. To achieve a sedative effect, dosages about 3 to 5 times the minimums of the above ranges are generally required. To achieve surgical sedation, intravenous infusion is preferred. Other routes of administration for these compositions are those commonly used by persons who are skilled in the pharmaceutical art, most preferably those used for the administration of acetaminophen.

From the foregoing description, one skilled in the art can easily ascertain the essential characteristics of this invention, and without departing from the spirit and scope thereof, can make various changes and modifications of the invention to adapt it to various usages and conditions. The following preferred specific embodiments are, therefore, to be construed as merely illustrative and not limitative of the disclosure in any way whatsoever.

EXAMPLE 1

In a conventional manner, fill gelatin capsules with, or prepare compressed tablets containing 250, 350 or 500 mg of N-ethyl-4'-hydroxyacetanilide or of N-isopropyl-4'-hydroxyacetanilide per capsule or tablet. Administer 1 to 2 capsules or tablets three or four times daily to an adult for relief of pain or fever, or both.

EXAMPLE 2

Prepare in alcoholic (8½%) mint-flavored and sweetened solution of 500, 750 or 1,000 mg of N-ethyl-4'-hydroxyacetanilide or of N-isopropyl-4'-hydroxyacetanilide (as its sodium salt) per fluid ounce (30 ml). Administer ⅜ fluid ounce up to 6 times daily or 1 fluid ounce up to 4 times daily, every 4–6 hours, for the relief of pain.

EXAMPLE 3

In a conventional manner, prepare sugar coated scored chewable fruit flavored tablets each containing 80 mg of N-ethyl-4'-hydroxyacetanilide or of N-isopropyl-4'-hydroxyacetanilide. Administer to children for pain, at a dosage of 1 or 2 tablets for children up to 3 years; 2 to 3 tablets for children of 4–5 years; 3 tablets for children of 6–8 years; and 4 tablets for children of 9–12 years, up to 3 to 4 times daily, for the relief of pain or fever, or both.

EXAMPLE 4–11

The following are further illustrations of the claimed compositions of this invention which have a lower incidence of hepatotoxic side effects than the corresponding compositions which contain acetaminophen.

| Form | N—ethyl- or N—isopropyl-4'-hydroxyacetanilide (mg) | Other Active Ingredients | Dosage | Times per Day |
|---|---|---|---|---|
| Suppository | 120 | — | 1 | up to 6 |
| Suppository (Ped.) | 60 | — | 1 | 1 |
| Tablets | 250 | Salicylamide (250) mg) | 1–2 | 4 |
| Tablets | 300 | Salicylamide (200 mg) Codiene phosphate (8 mg) Chlorpheniramine maleate (1 mg) | 1–2 | up to 6 |
| Tablets (scored) | 300 | Allobarbital (15 mg) | 1–2 | up to 4 |
| Tablets | 325 | Phenylpropanolamine HCl (18 mg) | 1–2 | up to 4 |
| Tablets | 300 | Chlorzoxazone (250 mg) | 2 | up to 4 |
| Elixir | 120/5 ml (Na salt) | — | 15 ml | up to 4 |

EXAMPLES 12–22

Follow the procedure of each of Examples 1–11, inclusive, but substitute the same amount of N-methyl-4-hydroxyacetanilide for the N-ethyl- or N-isopropyl-4'-hydroxyacetanilide employed therein. Although the resulting compositions are more prone to produce hepatotoxicity in highly susceptible persons at high dosages and over prolonged periods of time, than the compositions employed in Examples 1–11, they are far less prone to do so than the corresponding compositions containing the same amount of acetaminophen. Moreover, because they possess sedative and anti-inflammatory activity not possessed by the acetaminophen-based compositions, they can be used in situations in which the latter are not effective.

What I claim is:

1. A pharmaceutical composition comprising, in unit dosage form, an analgesic effective amount per unit dosage of an acetanilide compound of the formula

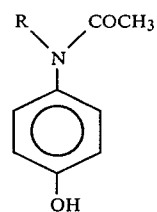

wherein R is methyl or branched or straight chain propyl, butyl, amyl, hexyl, heptyl, or octyl, in admixture with a pharmaceutically acceptable carrier.

2. A pharmaceutical composition according to claim 1 wherein the acetanilide compound is N-isopropyl-4'-hydroxyacetanilide.

3. A pharmaceutical composition according to claim 1, adapted for oral ingestion.

4. A pharmaceutical composition according to claim 3, in the form of a tablet or capsule.

5. A pharmaceutical composition according to claim 3, in the form of an aqueous solution.

6. A pharmaceutical composition according to claim 1, in the form of a sterile aqueous solution adapted for perenteral administration.

7. A pharmaceutical composition according to claim 2, adapted for oral ingestion.

8. A pharmaceutical composition according to claim 7, in the form of a tablet or capsule.

9. A pharmaceutical composition according to claim 2, in the form of a sterile aqueous solution adapted for perenteral administration.

10. A pharmaceutical composition according to claim 7, containing 100 to 500 mg per unit dosage of the acetanilide compound.

11. A pharmaceutical composition adapted for oral ingestion and in the form of a pill, tablet, capsule, dragree or sweetened syrup or elixir, comprising 150–1,000 mg per unit dosage of N-ethyl-4'-hydroxyacetanilide, in admixture with a pharmaceutically acceptable carrier.

12. A composition according to claim 11 in the form of a tablet or capsule containing 80–500 mg of N-ethyl-4'-hydroxyacetanilide.

13. A method for ameliorating pain which comprises administering to a human being in pain an analgesically effective amount of an acetanilide compound of the formula

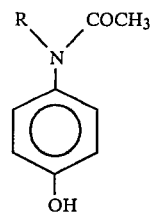

wherein R is alkyl of up to 8 carbon atoms, in admixture with a pharmaceutically acceptable carrier.

14. A method according to claim 13 wherein R is alkyl of 2 to 4 carbon atoms.

15. A method according to claim 13 wherein the acetanilide compound is N-ethyl-4'-hydroxyacetanilide.

16. A method according to claim 13 wherein the acetanilide compound is N-isopropyl-4'-hydroxyacetanilide.

17. A method according to claim 13 wherein the composition is adapted for oral ingestion and is administered orally.

18. A method according to claim 17 wherein the acetanilide compound is N-ethyl-4'-hydroxyacetanilide.

19. A method according to claim 17 wherein the acetanilide compound is N-isopropyl-4'-hydroxyacetanilide.

20. A method according to claim 13 wherein the composition is adapted for parenteral administration as is administered parenterally.

21. N-isopropyl-4'-hydroxyacetanilide.

* * * * *